(12) United States Patent
Cramer et al.

(10) Patent No.: US 6,630,668 B1
(45) Date of Patent: Oct. 7, 2003

(54) REMOTE CONTROL OF A SCANNING ELECTRON MICROSCOPE APERTURE AND GUN ALIGNMENT

(75) Inventors: Charles E. Cramer, Schenectady, NY (US); Robert J. Campchero, Schenectady, NY (US)

(73) Assignee: The United States of America as represented by the United States Department of Energy, Washington, DC (US)

(*) Notice: Subject to any disclaimer, the term of this patent is extended or adjusted under 35 U.S.C. 154(b) by 43 days.

(21) Appl. No.: 09/969,838

(22) Filed: Oct. 4, 2001

(51) Int. Cl.[7] .................. G01N 23/00; G21K 7/00; G21K 5/10; G02B 21/36; G02B 23/00; G02B 21/00; H01J 3/14; H01J 40/14; H01J 5/16
(52) U.S. Cl. ............. 250/310; 250/234; 250/306; 250/307; 250/309; 250/311; 250/442.11; 359/363; 359/384
(58) Field of Search .................. 250/310, 311, 250/440.11, 234, 306, 307, 309, 442.11; 359/363, 384

(56) References Cited

U.S. PATENT DOCUMENTS

| | | | |
|---|---|---|---|
| 4,807,966 A | 2/1989 | Nakayama et al. | |
| 5,001,824 A | * 3/1991 | Ayers | 29/436 |
| 5,455,420 A | 10/1995 | Ho et al. | |
| 5,510,615 A | 4/1996 | Ho et al. | |
| 5,652,676 A | * 7/1997 | Grinblat | 359/363 |
| 5,672,816 A | * 9/1997 | Park et al. | 73/105 |
| 5,780,853 A | * 7/1998 | Mori et al. | 250/310 |
| 5,805,335 A | * 9/1998 | Fukaya et al. | 359/384 |
| 5,836,694 A | 11/1998 | Nguyen | |
| 5,852,298 A | * 12/1998 | Hatakeyama et al. | 250/492.2 |
| 5,864,138 A | 1/1999 | Miyata et al. | |
| 5,945,684 A | 8/1999 | Lam et al. | |
| 6,064,060 A | * 5/2000 | Konada | 250/234 |

FOREIGN PATENT DOCUMENTS

EP 0510618 10/1992

* cited by examiner

Primary Examiner—John R. Lee
Assistant Examiner—Mary El-Shammaa
(74) Attorney, Agent, or Firm—Richard A. Morgan; Paul A. Gottlieb

(57) ABSTRACT

This invention relates to a remote control system which through gear motors coupled to the scanning electron microscope (SEM) manual control knobs readily permits remote adjustments as necessary.

27 Claims, 5 Drawing Sheets

REMOTE CONTROL OF A SCANNING ELECTRON MICROSCOPE APERTURE AND GUN ALIGNMENT

The U.S. Government has rights in this invention as provided for under the terms of a contract with the U.S. Department of Energy.

FIELD OF THE INVENTION

The present invention relates to a remote control system for use with a scanning electron microscope(SEM) to adjust aperture and gun alignment.

BACKGROUND OF THE INVENTION

In the past, scanning electron microscopes have used manual knob controls for adjusting the gun alignment as well as the aperture. Typically, electron microscopes disclosed in U.S. Pat. Nos. 5,864,138; 5,510,615 and 5,455,420 show manual knobs for adjustment mechanisms on electron microscopes. The European Patent No. 0510618A1 of Oct. 28, 1992, provides a remote control system for moving samples and also means for preventing leakage of x-rays and other radiation, but does not provide a remote system which can be attached directly to a manual control for operating remotely.

U.S. Pat. No. 4,807,966 shows a system for remote controlling of a sighting mechanism in an optical system. The motor control mechanism is built into the system. In general, remote control mechanisms are used in optical systems of various types such as illustrated in U.S. Pat. No. 5,836,694. The problem of adapting typical electron microscopes with manual systems so that they can be remotely controlled is not shown in the art.

OBJECTS AND SUMMARY OF THE INVENTION

It is an object of this invention to provide an electron microscope remote control system for the gun alignment and aperture which requires no internal modification of the typical Scanning Electron Microscope(SEM).

Another object of this invention is to provide remote control equipment for a SEM which is added to the exterior of the SEM so as to avoid any leakage of any radiation which might be caused by structural modifications of the SEM.

A further object of this invention is to provide a remote control for an electron microscope aperture and gun alignment which provides a high degree of safety and which can accomplish coarse or fine adjustment at a remote station.

Still a further object of this invention is to provide a remote control mechanism for the gun alignment and aperture which provides minimum backlash and allows for misalignment during adjustment.

Yet another object of this invention is to provide individual readouts for each adjustment motor and selection for each motor individually as well as means for controlling the speed of each motor adjustment means.

Still a further object of this invention is to provide a display and control panel for the remote system for the gun alignment and aperture which allows the operator to quickly make adjustment changes.

Another object of this invention is to provide a remote control system for the gun alignment and aperture that may be easily applied to a standard manual system of an electron microscope as well as easily removed therefrom as desired.

In summary, this invention relates to a remote control system for the gun alignment and aperture, which through gear motors coupled to the SEM manual control knobs, readily permits remote adjustments as necessary. This can be used on any commercially available SEM that adjusts the aperture and gun alignment in this manner.

These and other objects of the present invention will be apparent from the following description including the following drawings which are identified as follows:

BRIEF DESCRIPTIONS OF THE DRAWINGS

DETAILED DESCRIPTION OF THE INVENTION

Figure 1:
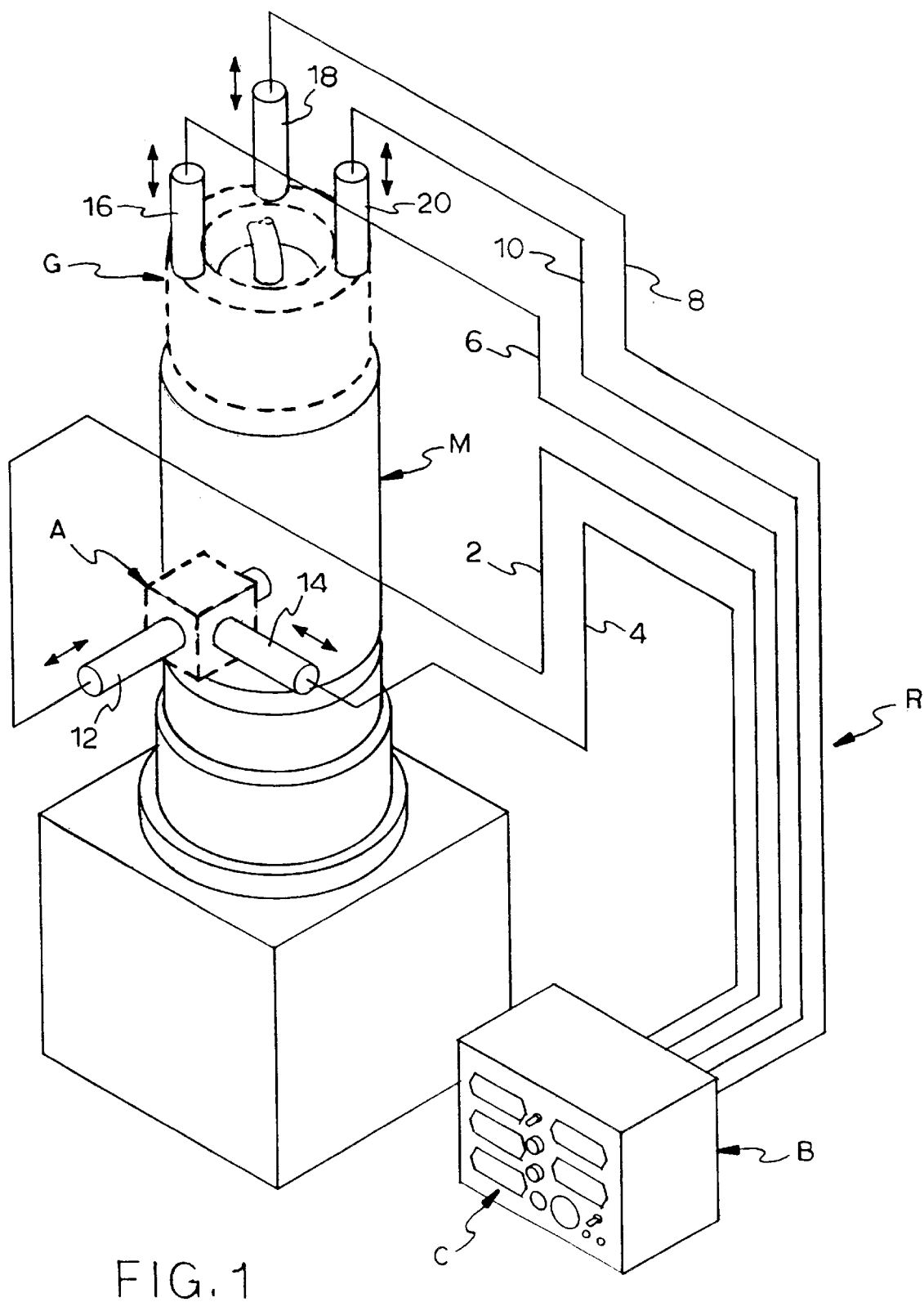
FIG. 1 is a schematic perspective view with portions shown in phantom lines which are subsequently shown in details in FIGS. 2, 3, 4, 5 and 6.

FIG. 1 shows schematically a portion of a SEM M. The remote system R includes a remote display and control panel box B with a display and control panel C. Electrical leads 2, 4, 6, 8 and 10 run from the remote display and control panel box B to a first motor drive unit A adapted to be mounted on the SEM M and a second motor drive unit G also adapted to be mounted on the SEM M for purposes hereinafter disclosed.

In FIG. 1, leads 2, 4, 6, 8 and 10 respectively run to drive motors 12, 14, 16, 18 and 20 as will be hereinafter described.

Figure 3:
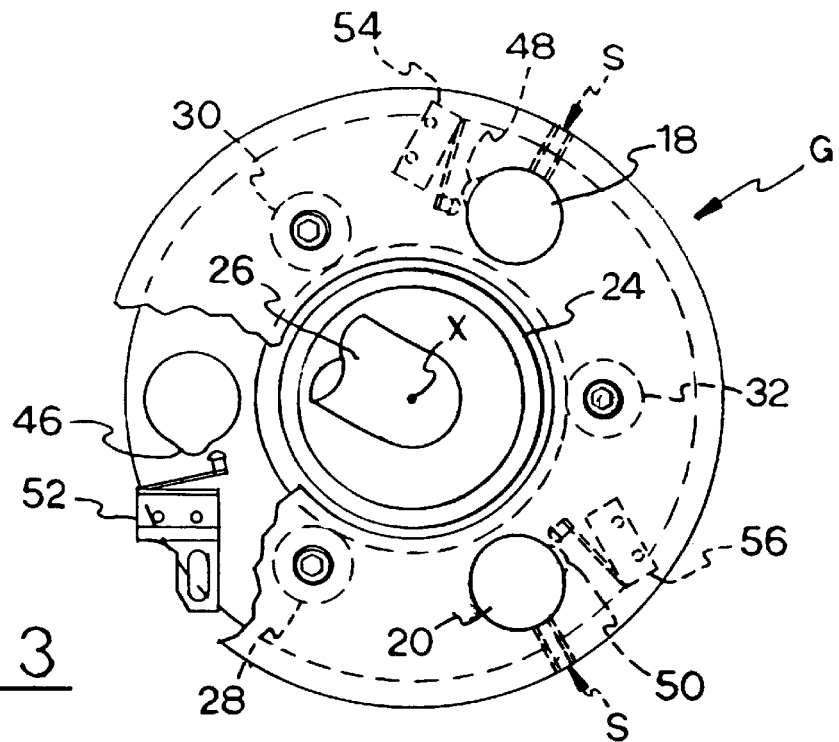
FIG. 3 is a top plan view with portions broken away and with portions shown with hidden lines of the mechanism shown in FIG. 2.
Figure 2:
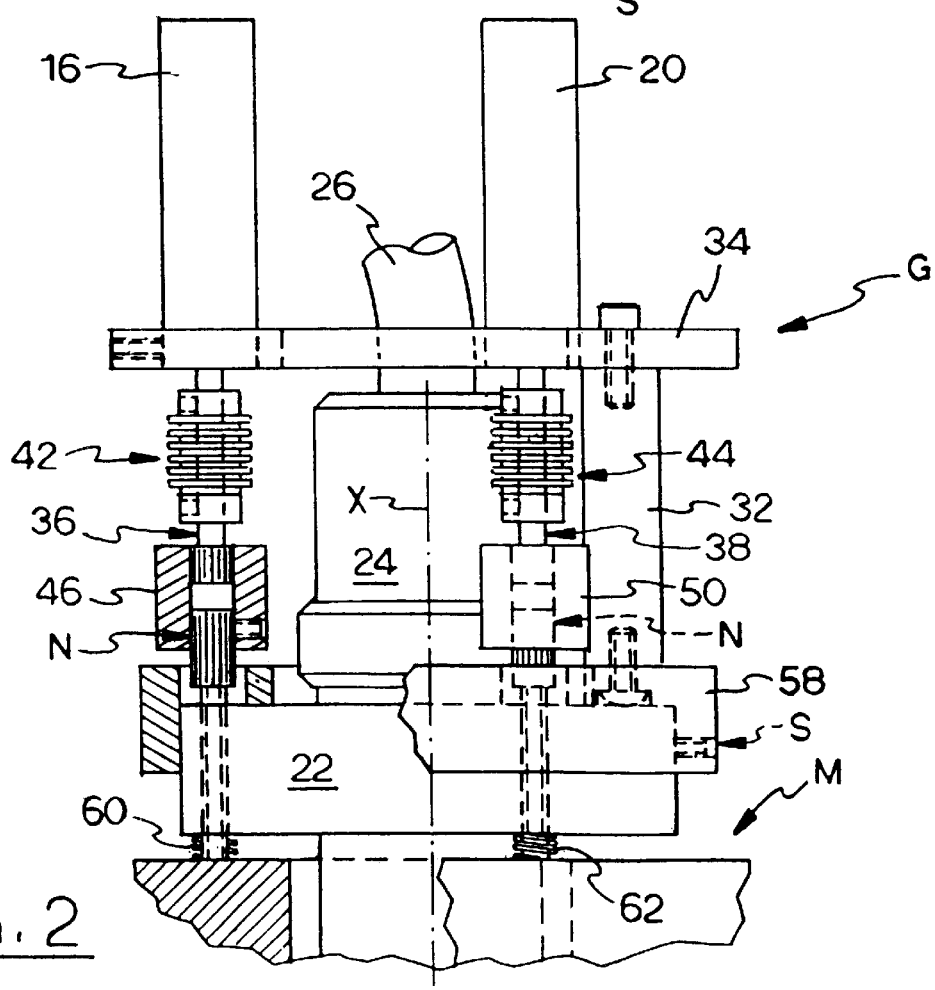
FIG. 2 is a fragmentary side elevational view with portions broken away of the gun alignment adjustment mechanism.

FIGS. 2 and 3

Referring now to FIGS. 2 and 3, the gun adjustment second motor drive unit G is shown mounted at the top of the SEM M. A collar 22 surrounds the electron gun 24 to which a power line 26 leads. Mounting pins 28, 30 and 32 secure an upper ring plate 34 to the lower ring plate 58. Drive motors 16, 18 and 20 are mounted on the upper ring plate 34. Motor drive shafts 36, 38 and 40 (not shown) each includes a bellows coupling such as 42 and 44 shown in FIG. 2. The bellows couplings are to correct for misalignment and backlash when a motor is driven. The motor drive shafts 36, 38 and 40 also include splined cams 46, 48 and 50 which operate against limit switches 52, 54 and 56. The limit switches 52, 54 and 56 may be bypassed by electrical controls (not shown). A lower ring plate 58 is mounted and secured to collar 22 by means of set screws S. Splined drive nuts N replace existing hand knobs and engage existing studs mounted on SEM M. Motor drive shafts 36, 38 and 40 couple to the splined drive nuts N by means of splined cams 46, 48 and 50. When rotated, the splined drive nuts N push against collar 22. Existing springs such as 60 and 62 press against the collar 22 and SEM M. Adjustment of the electron gun 24 will be about the axis X shown in FIG. 3 as controlled by the drive motors 16, 18 and 20 which operate on a 3 point basis to shift the gun 24 in the desired direction as needed depending upon which of the motors 16, 18 and 20 is driven.

Figure 4:
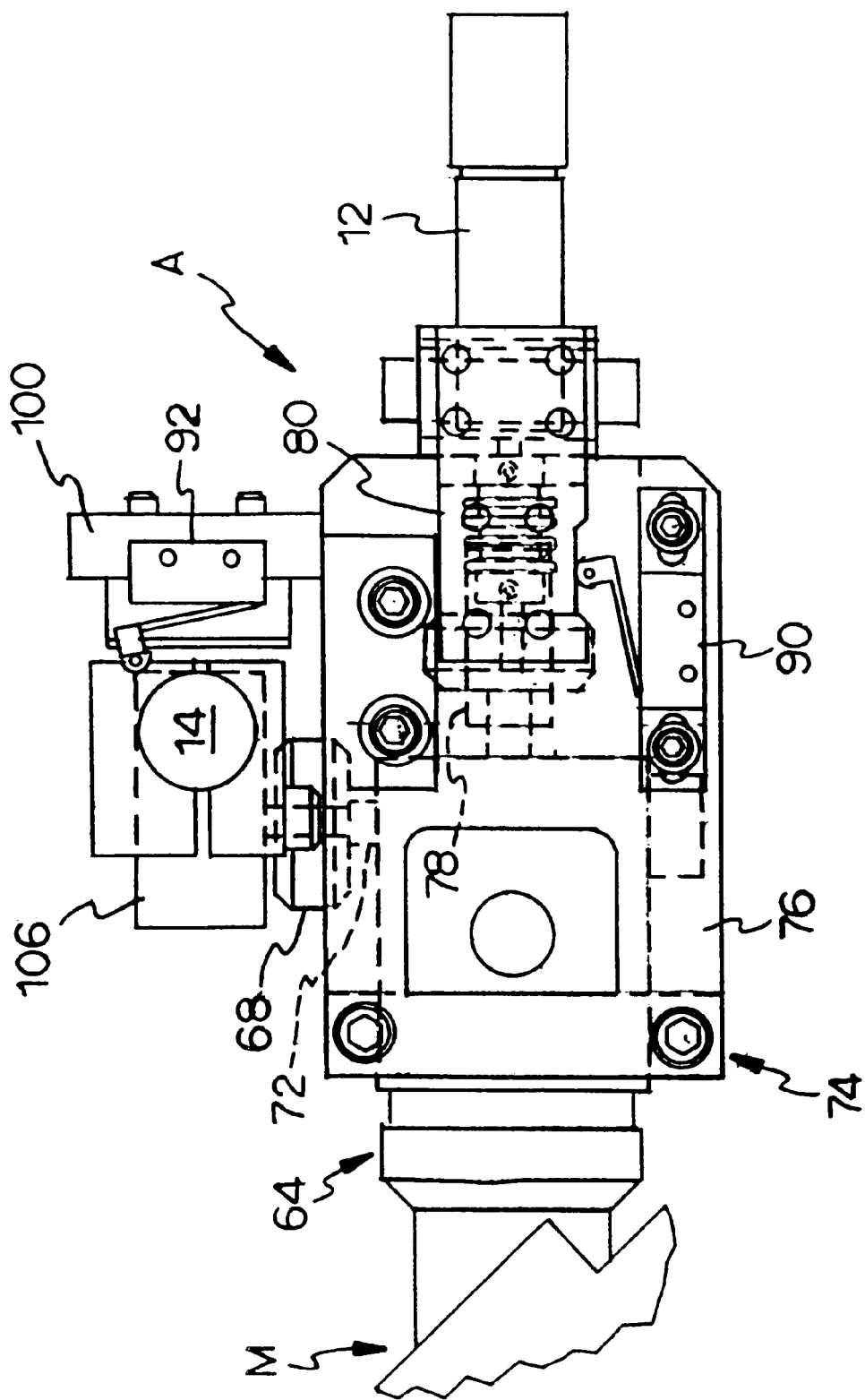
FIG. 4 is a top plan view of the aperture remote control in-and-out and side-to-side adjustment mechanism with portions shown in hidden lines.
Figure 6:
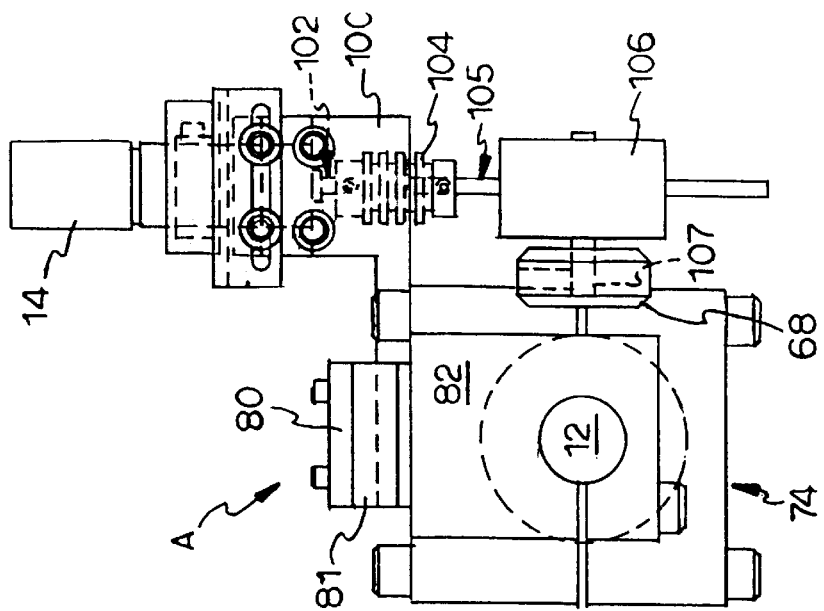
FIG. 6 is the right end elevational view of the aperture remote control mechanism shown in FIG. 4 with portions shown in phantom lines.
Figure 5:
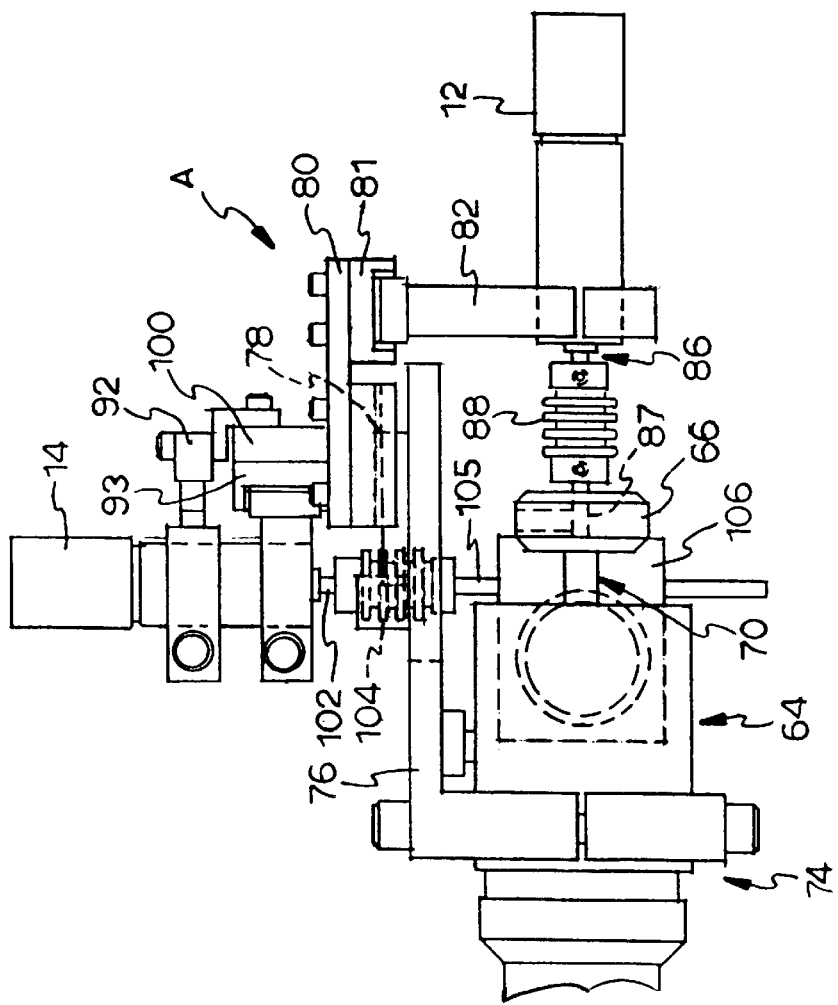
FIG. 5 is a side elevational view of the aperture remote control mechanism shown in FIG. 4.

FIGS. 4, 5 and 6

In FIGS. 4, 5 and 6, a motor drive unit A is provided for adjusting the aperture alignment of the SEM M. An aperture alignment mechanism 64 extends from the aperture (not shown) in the SEM M outwardly to a manual control knob 66 for controlling the in-and-out movement of the aperture. A side-to-side knob 68, as best shown in FIG. 4, controls side-to-side movement of the aperture (not shown). The knobs 66 and 68 are mounted on shafts 70 and 72 which are connected with the aperture alignment mechanism 64.

A clamp 74 secures a bracket.76 to the aperture alignment mechanism 64. Secured to the bracket 76 is a linear slide 78 the movable portion of which is attached to connecting arm 80. Connecting arm 80 is attached to linear slide 81 and is connected to a lateral extension arm 82. The extension arm 82 supports a drive motor 12 which has a drive shaft 86 secured to the shaft 87 extending from the knob 66 for in-and-out operation of the aperture (not shown). A bellows coupling 88 is mounted between the drive shaft 86 and shaft 87 to prevent backlash and allow for misalignment. A limit switch 90 mounted on the bracket 76 limits the travel of the drive motor 12. A limit switch 92 limits the travel of the motor 14 mounted on the linear slide 93 which is mounted on the bracket 100 which is attached to bracket 76.

The motor 14 has a drive shaft 102 which includes a bellows coupling 104. Bellows coupling 104 is attached to shaft 105 of right-angle gear box 106. When the motor 14 is activated, the drive shaft 102 drives the gears (not shown) in the right-angle gear box 106 to drive the shaft 107 which is attached to knob 68 to cause side-to-side motion to the aperture alignment mechanism 64 which in turn causes the aperture (not shown) to move side-to-side.

FIG. 7

Figure 7:
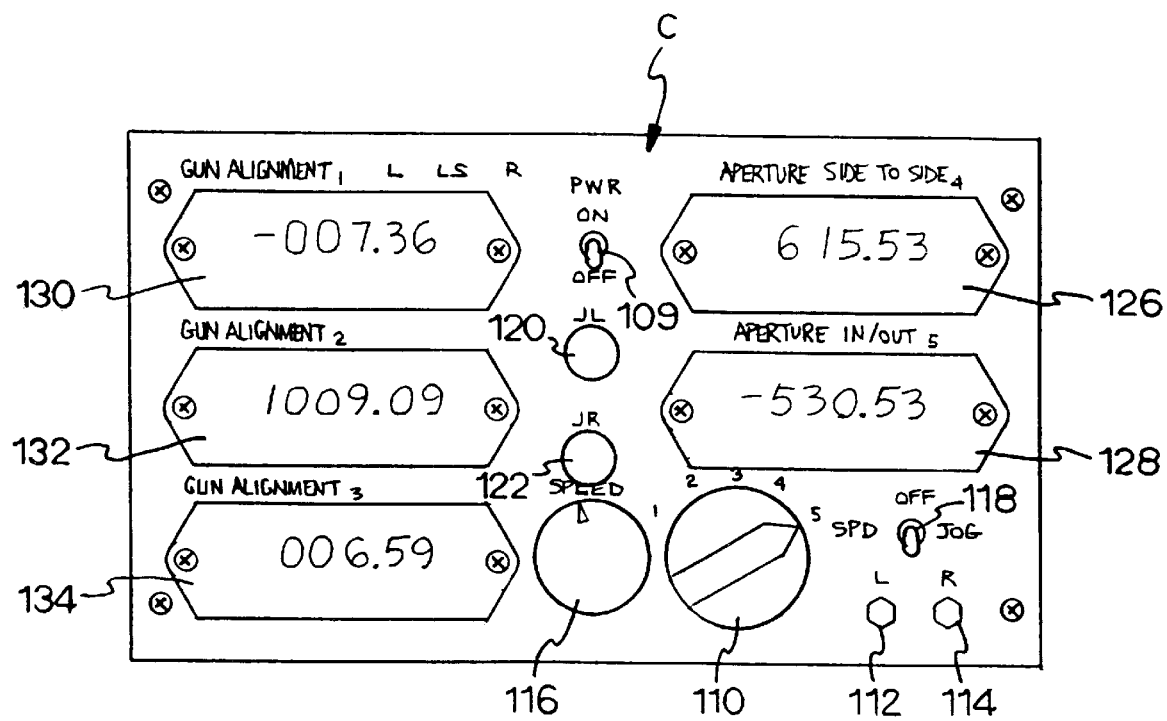
FIG. 7 is an enlarged front elevational view of the display and control panel of the display control panel box shown to the right in FIG. 1.

In FIG. 7, the display and control panel C includes a power on/off switch 109, a motor selector switch 110, a jog left push button 112, a jog right push button 114, a motor speed knob 116, an Off/Spd/Jog switch 118, a jog left speed knob 120, and a jog right speed knob 122. Aperture movement displays 126 and 128 are located on the right side of control panel C. Gun adjustment displays 130, 132 and 134 are located on the left side of the control panel C. As will be noted, printed above motor selector switch 110, there are position numbers 1, 2, 3, 4 and 5. These position numbers 1, 2, 3, 4 and 5 relate to gun alignment motors 16, 18 and 20 and aperture adjustment motors 12 and 14. Positioning motor selector switch 110 on position number 1, for example, allows motor 16 to be activated. Similarly positioning motor selector switch 110 on position number 4, for example, allows motor 12 to be activated. Thus, selected positioning of motor selector switch 110, activates the desired motor of motors 12, 14, 16, 18 and 20.

It is to be noted that, aperture movement displays 126 and 128 and gun adjustment displays 130, 132 and 134 have printed above them numbers 1, 2, 3, 4 and 5 which correspond to the numbers 1, 2, 3, 4 and 5 pointed above motor selector switch 110. Thus a visual readout of a motor position can be readily determined by the indicia showing up on the display as determined by the position of the motor selector switch 110.

In Operation

In operation, any one of the motors 12, 14, 16, 18 and 20 can be operated once the power switch 109 is turned on. To adjust a particular motor, e.g., motor 18, selector switch 110 is placed in position 2. For coarse adjustment the Off/Spd/Jog switch 118 is placed in the Spd position. The speed knob 116 is then rotated either clockwise or counter-clockwise from the midpoint. The motor 18 begins moving and the speed is increased as speed knob 116 is rotated farther. The relative distance traveled is shown on display 132. If fine adjustment is desired, the Off/Spd/Job switch 118 is placed in the Jog position. The JL 120 and JR 122 speed knobs are set at the desired speed. Then the L 112 or R 114 pushbuttons are depressed to achieve either clockwise or counter-clockwise rotation. Again, the relative distance traveled is shown on display 132.

It will now be obvious that the control of the aperture and the gun can be done remotely through the motor drives which operate through the remote display and control panel box B.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A remote control system, adapted to be connected to a SEM (scanning electronic microscope), said SEM having a movable aperture having longitudinal and transverse axes and a manual aperture alignment mechanism for moving said aperture on said longitudinal and transverse axes and having a movable electron gun having a longitudinal axis and a manual electron gun adjusting mechanism for moving said electron gun about said electron gun longitudinal axis, including:

a) a remote display and control panel;

b) a first motor drive unit adapted to be externally connected to said aperture alignment mechanism for moving said aperture alignment mechanism to cause said aperture to move on said aperture longitudinal and transverse axes;

c) a second motor drive unit adapted to be externally connected to said electron gun adjusting mechanism for moving said electron gun adjusting mechanism to cause said electron gun to move about said electron gun longitudinal axis;

d) said first and second motor drive units each having forward and reverse drives;

e) said first and second motor drive units connected to said remote display and control panel;

f) said display control panel having separate displays for said first and second motor drive units;

g) said display and control panel having a power ON/OFF switch, a selector control for powering either said first or said second motor drive units when said ON/OFF switch is on, a speed control for said first and second motor drive units, and forward and reverse direction controls for said first and second motor drive units;

h) said display control panel separate displays having changeable readout indicia indicating the direction and amount of travel of said aperture during and after alignment and of said gun during and after adjustment during and after actuation of said first and second motor drive units.

2. A remote control system as in claim 1 and wherein:
a) said display and control panel includes course and fine speed control for said direction controls.

3. A remote control system as in claim 1 and wherein:
a) said display and control panel includes repeat speed setting controls for subsequent operation of said remote control system at previously established settings.

4. A remote control system as in claim 1 and wherein:
a) said first motor drive unit includes an in/out motor and a side-to-side motor.

5. A remote control system as in claim 1 and wherein:
a) said second motor drive unit includes three separate motors individually driveable and arranged about said electron gun to permit said gun to be adjusted about said electron gun longitudinal axis when a motor is actuated.

6. A remote control system as in claim 4 and wherein:
a) said separate display for said first motor drive unit includes a readout display for said in/out motor and a readout display for said side-by-side motor.

7. A remote control system as in claim 5 and wherein:
a) said separate display for said second motor drive unit includes a readout display for each of said three separate motors.

8. A remote control system as in claim 1 and wherein:
a) said first and second motor drive units each include devices to minimize backlash and allow for misalignment.

9. A remote control system as in claim 8 and wherein:
a) said backlash and misalignment devices include bellows couplings.

10. A remote control system as in claim 5 and wherein:
a) said three separate motors are mounted on a collar adapted to be positioned about said electron gun.

11. A remote control system as in claim 4 and wherein:
a) said in/out motor and said side-to-side motor are mounted on a single electron gun mount bracket and are adjustable relative to each other.

12. A remote control system, adapted to be connected to a SEM (scanning electronic microscope) having a movable aperture having longitudinal and transverse axes and a manual aperture alignment mechanism for moving said aperture, including:
a) a remote display and control panel;
b) a motor drive unit adapted to be externally connected to said aperture alignment mechanism for moving said aperture alignment mechanism to cause said aperture to move on said aperture longitudinal and transverse axes;
c) said motor drive unit having forward and reverse drive;
d) said motor drive unit connected to said remote display and control panel;
e) said display and control panel having separate displays for said motor drive unit;
f) said display control panel having a power on/off switch, a selector control for powering said first motor drive unit when said on/off is on, a speed control for said motor drive unit and forward and reverse direction controls for said motor drive unit;
g) said display and control panel separate displays having changeable readout indicia indicating the direction and amount of travel of said aperture during and after alignment during and after actuation of said motor drive unit.

13. A remote control system as in claim 12 and wherein:
a) said display and control panel includes coarse and fine speed control for said direction controls.

14. A remote control system as in claim 12 and wherein:
a) said display and control panel includes repeat speed setting controls for subsequent operation of said remote control system at previously established settings.

15. A remote control system as in claim 12 and wherein:
a) said motor drive unit includes an in/out motor and a side-to-side motor.

16. A remote control system as in claim 15 and wherein:
said separate display for said motor drive unit includes a readout display for said in/out motor and a readout display for said side-by-side motor.

17. A remote control system as in claim 12 and wherein:
a) said motor drive unit includes devices to minimize backlash and allow for misalignment.

18. A remote control system as in claim 17 and wherein:
a) said backlash and misalignment devices include bellows couplings.

19. A remote control system as in claim 15 and wherein:
a) said in/out motor and said side-to-side motor are mounted on a single electron gun mount bracket and are adjustable relative to each other.

20. A remote control system adapted to be connected to a SEM (scanning electron microscope) having a moveable electron gun having a longitudinal axis and a manual electron gun adjusting mechanism for moving said electron gun about said electron gun longitudinal axis, including:
a) a remote display and control panel;
b) a motor drive unit adapted to be externally connected to said electron gun adjusting mechanism removing said electron gun mechanism to cause said electron gun to move about said electron gun longitudinal axis;
c) said motor drive unit having forward and reverse drive;
d) said motor drive unit connected to said display and control panel;
e) said display and control panel having separate displays for said motor drive unit;
f) said display and control panel having a power on/off switch, a selector control for powering said motor drive unit when said on/off switch is on, a speed control for said motor drive unit and forwarding reverse direction controls for said motor drive unit;
g) said display and control panel separate display having changeable readout indicia indicating the direction and amount of travel of said gun during and after adjustment during and after actuation of said motor drive unit.

21. A remote control system as in claim 20 and wherein:
a) said display and control panel includes coarse and fine speed controls for said direction controls.

22. A remote control system as in claim 20 and wherein:
a) said display and control panel includes repeat speed setting controls for subsequent operation of said remote control system at previously established settings.

23. A remote control system as in claim 22 and wherein:
a) said motor drive unit includes three separate motors individually driveable and arranged about said electron gun to permit said gun to be adjusted about said electron gun longitudinal axis when a motor is actuated.

24. A remote control system as in claim 20 and wherein:
a) said separate display for said motor drive unit includes a readout display for each of said three separate motors.

25. A remote control system as in claim 20 and wherein:
a) said motor drive unit includes devices to minimize backlash and allow for misalignment.

26. A remote control system as in claim 25 and wherein:
a) said backlash and misalignment devices includes bellows couplings.

27. A remote control system as in claim 23 And wherein:
a) said three separate motors are mounted on a collar adapted to be positioned about said electron gun.

* * * * *